(12) United States Patent
Irving et al.

(10) Patent No.: US 6,430,536 B2
(45) Date of Patent: *Aug. 6, 2002

(54) METHOD AND SYSTEMS FOR ASSET MANAGEMENT

(75) Inventors: Russell Robert Irving, Balston Lake, NY (US); Samantha Allison Ploof, Pewaukee, WI (US)

(73) Assignee: General Electric Company, Schenectady, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/435,551

(22) Filed: Nov. 8, 1999

Related U.S. Application Data (63) Continuation of application No. 08/848,108, filed on Apr. 28, 1997, now abandoned.

(51) Int. Cl.[7] ............................................... G06F 17/60
(52) U.S. Cl. .......................................................... 705/2
(58) Field of Search .................................. 705/2, 7, 8, 9, 705/10, 28, 29; 700/99, 100

(56) References Cited

U.S. PATENT DOCUMENTS

| | | | | |
|---|---|---|---|---|
| 5,289,370 A | * | 2/1994 | Lirov | 705/8 |
| 5,450,317 A | * | 9/1995 | Lu et al. | 705/10 |
| 5,724,262 A | * | 3/1998 | Ghahramani | 702/186 |
| 5,778,345 A | * | 7/1998 | McCartney | 705/2 |
| 5,946,662 A | * | 8/1999 | Ettl et al. | 705/8 |
| 5,960,414 A | * | 9/1999 | Rand et al. | 705/28 |
| 5,963,910 A | * | 10/1999 | Ulwick | 705/7 |
| 5,963,919 A | * | 10/1999 | Brinkley et al. | 705/28 |
| 5,991,728 A | * | 11/1999 | DeBusk et al. | 705/2 |
| 6,012,041 A | * | 1/2000 | Brewer et al. | 705/28 |
| 6,049,774 A | * | 4/2000 | Roy | 705/8 |
| 6,092,060 A | * | 7/2000 | Guinta et al. | 706/47 |

OTHER PUBLICATIONS

Pfohl, H. 'Inventory Management with Statistical Process Control: Simulation and Evaluation', Journal of Business Logistics, v20, n1, pp. 100–120, 1999. File 15: ABI/Inform ® Dialog Accession # 0196756.*

Blumberg, D.F., 'Strategic Benchmarking of Service and Logistic Support Operations', Journal of Business Logistics, v15, n2, pp. 89–119, 1994. File 15: ABI/Inform ® Dialog Accesssion #00916127.*

* cited by examiner

Primary Examiner—Richard Chilcot
Assistant Examiner—Jennifer Harle
(74) Attorney, Agent, or Firm—Carl B. Horton, Esq.; Armstrong Teasdale LLP (57) ABSTRACT

Methods and systems for generating reports with respect to medical imaging equipment of a health care organization are described. In accordance with one embodiment of the present invention, a processor based system is configured to prompt a user to collect various data related to a number of facilities. The data typically relates to the equipment, or inventory, as well as to the various types of procedures, and the number of procedures, performed at the facility. After collecting the necessary data, the system then determines, or calculates, various summaries, assessments, capacity utilization, needs assessment, needs comparison, equipment requirements comparison, and procedural efficiency. After making such determinations, the system builds and formats various reports and graphs for presenting the determinations to the user.

14 Claims, 14 Drawing Sheets

| Facility | Modality | Equip. Model (Yr.) | Utilization | Options | 3 Yr EBITDA |
|---|---|---|---|---|---|
| *EXCESS CAPACITY* | | | | | |
| Facility A | Portables | MobileMaster (92) | 25% | Leave as is | |
| | Portables | MobilePro (92) | | Leave as is | |
| | Portables | XR4000 (90) | | Leave as is | |
| | Portables | XR200 (84) | | Leave as is | |
| | Portables | XR50 (unavailable) | | Scrap | $12,000 |
| *CONSTRAINED CAPACITY* | | | | | |
| Facility A | CT | CTSupreme Plus (91) | 122% | Add a unit | $200,000 |
| | Specials | SuperStar (95) | 81% | Extend Hrs. | $37,000 |

*FACILITY COMMENTS*

■ Portable utilization is 25%. Scrap one (1) unit to reduce service cost, allows the other 4 units to be dedicated to specific areas.

■ 23% growth in CT procedures is projected over the next five (5) years. Add a unit with Helical capabilities to reduce capacity constraints and allow for growth capture.

■ Extending the hours of operation in Special procedures will increase capacity. Consider adding a unit when capacity fills extended hours.

■ Increased growth is anticipated in U/S procedures. Ultrasound is approaching capacity. Current equipment has limited technology. Consider upgrading one unit to increase functionality and capacity.

■ 16% growth in RAD/R&F procedures is projected over the next five (5) years. RAD/R&F is approaching capacity. Current equipment has limited technology. Consider upgrading one unit to increase functionality and capacity.

FIG. 8

| Equipment Type | Total Units In Use | Market Capacity Utilization | Recommendation | 3 year EBITDA | Equipment Capital Investment | 3 Year Cash Flow |
|---|---|---|---|---|---|---|
| CT | 14 | 71% | 2 - Add a unit<br>5 - Upgrade<br>3 - Replace<br>1 - Extend hours | $450,000<br>$2,500,000<br>$2,450,000 | $2,000,000<br>$4,825,000<br>$2,500,000 | ($1,550,000)<br>($2,325,000)<br>($50,000) |
| MRI | 9 | 57% | 1 - Upgrade/Replace<br>1 - Extend hours | $300,000<br>$200,000 | $1,750,000<br>$0 | ($1,450,000)<br>($200,000) |
| Nuclear Medicine | 17 | 50% | 1 - Upgrade/Replace<br>1 - Add a unit | $85,000<br>$70,000 | $800,000<br>$800,000 | ($515,000)<br>($530,000) |
| Portables | 30 | 25% | 4 - Scrap | $65,000 | $0 | $65,000 |
| Ultrasound | 24 | 62% | 5 - Add a unit<br>1 - Upgrade/Replace | $385,500<br>$260,000 | $1,000,000<br>$200,000 | ($614,500)<br>$60,000 |
| R&F | 13 | 74% | 2 - Upgrade & add unit<br>2 - Upgrade/Replace | $560,000<br>$265,000 | $1,500,000<br>$450,000 | ($940,000)<br>($185,000) |
| Mammography | 19 | 56% | 1 - Upgrade<br>1 - Extend hours | $95,000<br>($12,500) | $75,000<br>$0 | $20,000<br>($12,500) |
| RAD | 37 | 74% | 10 - Upgrade/Replace<br>2 - Scrap<br>6 - Add a unit | $3,500,000 | $4,000,000 | ($500,000) |
| Specials | 7 | 49% | 1 - Scrap<br>1 - Extend hours | $50,000<br>$37,000 | $0<br>$0 | $50,000<br>$37,000 |
| | | | TOTALS | $11,260,000 | $19,500,000 | ($8,240,000) |

FIG. 9

|  | | CT | | | | MR | | | |
|---|---|---|---|---|---|---|---|---|---|
|  | Units | Inpatient | Outpatient | ER | Total/Unit | Units | Inpatient | Outpatient | ER | Total/Unit |
| FACILITY A |  | 741 42.3% | 1,009 57.7% | 0 0.0% | 1,750 |  |  |  |  |  |
| FACILITY B |  |  |  |  |  |  |  |  |  |  |
| FACILITY C | 1 | 2,942 39.3% | 3,895 52.0% | 653 8.7% | 7,490 | 1 | 377 21.4% | 1,352 76.9% | 30 1.7% | 1,759 |
| FACILITY D | 1 | 525 45.4% | 468 40.5% | 163 14.1% | 1,156 | 1 | 127 | 399 | 6 | 532 |
| FACILITY E | 2 | 1,573 40.3% | 1,779 45.6% | 548 14.1% | 3,899 | 1 | 534 17.0% | 2,610 82.9% | 6 0.2% | 3,150 |
| FACILITY F | 1 | 2,844 39.8% | 3,392 47.4% | 915 12.8% | 7,151 | 1 | 335 20.0% | 1,343 80.0% | 0 0.0% | 1,678 |
| FACILITY G |  |  |  |  |  |  |  |  |  |  |
| FACILITY H | 1 | 974 56.7% | 744 43.3% | 0 0.0% | 1,718 |  |  |  |  |  |
| FACILITY I | 1 | 527 35.7% | 949 64.3% | 0 0.0% | 1,476 |  |  |  |  |  |
| FACILITY J | 1 | 589 41.3% | 554 38.9% | 282 19.8% | 1,425 |  |  |  |  |  |
| FACILITY K |  |  |  |  |  |  |  |  |  |  |
| FACILITY L | 1 | 757 33.2% | 1,523 66.8% | 0 0.0% | 2,280 |  |  |  |  |  |
| FACILITY M | 1 | 1,524 35.9% | 2,725 64.1% | 0 0.0% | 4,249 | 1 | 305 26.5% | 846 73.5% | 0 0.0% | 1,151 |
| FACILITY N | 1 | 1,675 45.1% | 1,630 43.9% | 408 11.0% | 3,713 | 1 | 181 | 726 | 16 | 923 |
| FACILITY O | 1 | 1,676 51.0% | 1,613 49.0% | 0 0.0% | 3,289 | 1 | 445 44.9% | 545 55.1% | 0 0.0% | 990 |
| FACILITY P | 1 | 862 32.5% | 1,789 67.5% | 0 0.0% | 2,651 | 1 | 183 13.4% | 1,179 86.6% | 0 0.0% | 1,362 |
| FACILITY Q | 1 | 3,026 35.8% | 4,552 53.9% | 867 10.3% | 8,445 | 1 | 960 31.3% | 2,067 67.4% | 41 1.3% | 3,068 |
| FACILITY R |  | 0 0.0% | 317 100.0% | 0 0.0% | 317 | 1 | 0 0.0% | 1,092 100.0% | 0 0.0% | 1,092 |
| FACILITY S | 1 | 57 5.5% | 975 94.5% | 0 0.0% | 1,032 | 1 | 47 2.3% | 1,918 95.8% | 38 1.9% | 2,003 |

| Units | Inpatient | | Outpatient | | ER | | Total/Unit |
|---|---|---|---|---|---|---|---|
| | | | NUC. MED | | | | |
| 1 | 202 | 44.5% | 252 | 55.5% | 0 | 0% | 454 |
| 2 | 674 | 37.4% | 1,091 | 60.5% | 39 | 2.2% | 1,804 |
| 1 | 187 | 52.7% | 155 | 43.7% | 13 | 3.7% | 355 |
| 6 | 517 | 35.0% | 945 | 64.0% | 15 | 1.0% | 1,477 |
| 3 | 924 | 52.3% | 842 | 47.7% | 0 | 0.0% | 1,766 |
| 1 | 422 | 65.8% | 219 | 34.2% | 0 | 0.0% | 641 |
| 1 | 273 | 46.8% | 310 | 53.2% | 0 | 0.0% | 583 |
| 1 | 229 | 40.7% | 255 | 45.4% | 78 | 13.9% | 562 |
| 2 | 345 | 46.9% | 391 | 53.1% | 0 | 0.0% | 735 |
| 1 | 1,494 | 50.9% | 1,441 | 49.1% | 0 | 0.0% | 2,935 |
| 1 | 449 | 41.3% | 614 | 56.5% | 24 | 2.2% | 1,087 |
| 2 | 600 | 53.6% | 520 | 46.4% | 0 | 0.0% | 1,120 |
| 1 | 408 | 32.2% | 858 | 67.8% | 0 | 0.0% | 1,266 |
| 3 | 801 | 47.4% | 873 | 51.5% | 16 | 1.1% | 1,690 |

| EXAM NAME | Total Procedures | Avg. Mkt. Time | Std. Time | Mkt. Std. Spread | Potential Additional Procedures | % Additional Procedures |
|---|---|---|---|---|---|---|
| CT EXAMS | | | | | | |
| BRAIN WO | 13117 | 23.3 | 15 | 8.3 | 7287 | 56% |
| ABDOMEN W/WO | 7490 | 62.5 | 60 | 2.5 | 312 | 4% |
| PELVIS W | 5470 | 46.3 | 20 | 26.3 | 7187 | 131% |
| CHEST/THORAX W | 3735 | 46.7 | 35 | 11.7 | 1245 | 33% |
| BRAIN W/WO | 3709 | 42.5 | 35 | 7.5 | 795 | 21% |
| ABDOMEN W | 2491 | 46.1 | 35 | 11.1 | 791 | 32% |
| ABDOMEN WO | 2199 | 43.6 | 35 | 8.6 | 541 | 25% |
| PELVIS WO | 1848 | 40.3 | 20 | 20.3 | 1874 | 101% |
| | | | | | | |
| MAMMOGRAPHY PROCEDURES | | | | | | |
| MAMMOGRAM DIAGNOSTIC BILATERAL | 34998 | 37.0 | 30 | 7.0 | 8204 | 23% |
| MAMMOGRAM SCREEN BILATERAL | 8114 | 30.7 | 30 | 0.7 | 201 | 2% |
| MAMMOGRAM SCRN BILAT & EDUCATION | 4268 | 44.4 | 45 | -0.6 | -61 | -1% |
| MAMMOGRAM DIAGNOSTIC UNILATERAL | 2195 | 26.0 | 20 | 6.0 | 659 | 30% |
| BREAST NEEDLE LOCALIZATION | 645 | 57.3 | 50 | 7.3 | 94 | 15% |
| BREAST SURGICAL SPECIMEN | 190 | 20.0 | 20 | 0.0 | 0 | 0% |
| | | | | | | |
| MRI EXAMS | | | | | | |
| BRAIN WITHOUT | 2643 | 51.3 | 21 | 30.3 | 3807 | 144% |
| BRAIN W/WO | 1925 | 54.8 | 28 | 26.8 | 1839 | 96% |
| EXTREMITY (LOWER) INCL. JOINT | 1778 | 61.8 | 42 | 19.8 | 840 | 47% |
| C-SPINE | 1689 | 57.3 | 56 | 1.3 | 37 | 2% |
| BRAIN WITH | 1275 | 49.7 | 21 | 28.7 | 1740 | 137% |
| ABDOMEN | 954 | 59.3 | 21 | 38.3 | 1741 | 183% |
| EXTREMITY (UPPER) INCL. JOINT | 629 | 60.0 | 35 | 25.0 | 449 | 71% |
| | | | | | | |
| NUCLEAR MEDICINE EXAMS | | | | | | |
| BONE SCAN | 5077 | 61.3 | 60 | 1.3 | 106 | 2% |
| MYOCARDIAL PERFUSION SPECT STRESS | 4363 | 40.6 | 30 | 10.6 | 1545 | 35% |
| COMPUTER ANALYSIS-LESS THAN 30 MIN. | 4060 | 29.5 | 30 | -0.5 | -63 | -2% |
| MYOCARDIAL PERFUSION SPECT REST | 2650 | 35.6 | 30 | 5.6 | 497 | 19% |
| LUNG PERFUSION | 2647 | 33.6 | 30 | 3.6 | 317 | 12% |
| LUNG VENT OR XENON VENT | 2468 | 17.7 | 10 | 7.7 | 1890 | 77% |
| COMPUTER ANALYSIS-MORE THAN 30 MIN. | 1294 | 46.1 | 45 | 1.1 | 31 | 2% |

FIG. 11

| EXAM NAME | FACILITY A | FACILITY B | FACILITY C | FACILITY D | FACILITY E | FACILITY F | FACILITY G | FACILITY H | FACILITY I | FACILITY J | FACILITY K | FACILITY L | FACILITY M |
|---|---|---|---|---|---|---|---|---|---|---|---|---|---|
| RAD EXAMS | | | | | | | | | | | | | |
| CHEST PA & 1 LAT | | 20 | 25 | 10 | 13 | 30 | 15 | 10 | 15 | 8 | 15 | 20 | 12 |
| CHEST AP ONLY | | | 15 | 10 | | 25 | | 10 | 15 | 8 | | 15 | 11 |
| ABDOMEN AP | | 15 | 15 | 15 | 10 | | 15 | 10 | 15 | 8 | 10 | 15 | |
| ABDMN AP & UPRT & CHEST | | | 30 | 20 | 15 | 40 | 25 | 20 | 20 | 12 | 25 | 30 | 22 |
| L-SPINE AP/LAT/2 OBL/SPOT | | 40 | 30 | 30 | 20 | 30 | 25 | 20 | 20 | 26 | 25 | 40 | 22 |
| ANKLE AP/LAT/1 OBLQ | | 20 | 30 | 15 | 10 | 25 | 15 | 10 | 15 | 15 | 15 | 15 | 10 |
| IVP W/KUB & TOMOGRAMS | | | | 45 | 60 | 80 | 45 | 60 | 50 | 35 | 60 | 120 | 70 |
| FOOT | | | | 15 | 10 | 25 | | 10 | 15 | 10 | 15 | | 10 |
| SKULL COMPLETE 4 VIEW | | 45 | 40 | 20 | 15 | | 20 | 15 | 20 | 20 | | 30 | 18 |
| | | | | | | | | | | | | | |
| SPECIALS EXAMS | | | | | | | | | | | | | |
| ABDOMINAL AORTOGRAM | | 30 | | | 60 | | | | | | | 60 | 70 |
| FLUOROSCOPIC GUIDANCE | | | | 60 | | | | | | | | | 90 |
| CAROTID CERVICAL, BILATERAL | | 40 | | 135 | 120 | | | | | | 120 | | 150 |
| CAROTID CEREBRAL, UNILATERAL | | | | 100 | 90 | | | | | | 120 | | 130 |
| EACH ADDITIONAL VESSEL AFTER BASIC | | | | 30 | 60 | | | | | | | | |
| | | | | | | | | | | | | | |
| ULTRASOUND EXAMS | | | | | | | | | | | | | |
| ABDOMEN | 60 | | | 60 | 60 | 25 | 25 | 45 | 30 | 45 | 60 | 60 | 48 |
| PELVIC COMPLETE | 45 | | 45 | 40 | 45 | | 30 | 45 | 25 | 45 | 40 | 60 | 50 |
| OBSTETRICS COMPLETE | | | | 60 | 60 | 40 | 40 | 60 | 45 | | 60 | 60 | 60 |
| GALLBLADDER | 30 | 30 | 45 | 35 | 45 | 20 | 20 | 30 | 20 | 30 | 45 | 45 | |
| TRANSVAGINAL | 60 | 30 | 45 | 45 | 45 | 20 | | 45 | 15 | 30 | 60 | 60 | 55 |
| BREAST | 30 | | | 35 | 30 | 20 | 20 | 15 | 15 | 30 | 30 | 45 | 35 |
| RENAL | 30 | 45 | | 35 | 30 | 25 | 20 | 20 | | | 45 | 40 | 40 |
| CAROTID DUPLEX | | | 60 | 60 | | | 30 | 60 | 45 | | | | 65 |
| VENOUS UPPER/LOWER EXTREMITY DUP | 30 | | | 60 | | | 45 | 60 | 30 | | | | 68 |

| FACILITY N | FACILITY O | FACILITY P | FACILITY Q | FACILITY R |
|---|---|---|---|---|
|  |  |  |  |  |
|  |  |  |  |  |
| 15 | 10 |  | 20 | 15 |
|  | 5 |  | 10 | 11 |
| 10 | 15 |  | 15 | 11 |
| 20 | 25 |  |  |  |
| 15 | 30 |  | 25 | 30 |
| 15 | 15 |  | 20 | 20 |
| 60 | 60 |  | 60 | 45 |
| 15 | 10 |  | 10 | 20 |
| 15 | 20 |  | 30 |  |
|  |  |  |  |  |
|  |  |  |  |  |
| 120 |  |  | 90 |  |
|  |  |  | 60 |  |
|  |  |  | 160 |  |
| 120 |  |  | 15 |  |
| 45 |  |  | 10 |  |
|  |  |  |  |  |
|  |  |  |  |  |
| 60 | 45 | 30 | 45 | 40 |
| 60 | 25 | 30 | 30 |  |
| 60 | 75 |  | 60 | 45 |
| 35 |  | 30 |  | 40 |
| 60 | 25 |  | 30 |  |
| 45 | 40 |  | 30 |  |
| 45 | 45 | 30 | 30 | 40 |
|  |  |  |  | 75 |
| 60 | 75 | 30 | 35 | 50 |

METHOD AND SYSTEMS FOR ASSET MANAGEMENT

CROSS REFERENCE TO RELATED APPLICATIONS

This application is a continuation of U.S. patent application Ser. No. 08/848,108, filed Apr. 28, 1997, now abandoned entitled "Methods and Systems for Asset Management," which is incorporated by reference herein in its entirety.

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

This invention relates generally to asset management and, more particularly, to methods and systems for assisting health care organizations to manage medical imaging equipment inventories and usage.

Management health care costs has been the focus of many health care organizations. Although the costs associated with medical imaging equipment are significant for at least some health care organizations, there currently is no known systems or methods for facilitating automated analysis to facilitate identifying the optimum use of such equipment. For example, a hospital or clinic typically has a mix of imaging equipment, such as CT, MRI, and X-Ray machines. For each machine, numerous procedures can be performed, and for each procedure, there typically is a desired completion time. Until now, no known systems or methods perform a substantially automated analysis to facilitate determinations with respect to whether the imaging equipment is being used in an optimum manner. Without such systems and methods, health care organizations may have extreme difficulty in improving and achieving optimum efficiency in its use of imaging equipment.

In addition, there currently are no known systems and methods which facilitate managing imaging assets. Particularly, in order to determine present and future equipment needs, it would be desirable to provide systems and methods for forecasting future patient and procedure volumes, and then, using such forecasts, facilitate determining future equipment needs. Of course, in making such determinations, the current imaging equipment inventory and efficiency should be known.

It would be desirable to provide automated systems or methods for analyzing imaging equipment usage so that health care organizations can attempt to optimize equipment usage. It also would be desirable to provide such systems and methods which facilitate managing imaging assets, including forecasting future patient and procedure volumes.

BRIEF SUMMARY OF THE INVENTION

These and other objects may be attained by a system for generating reports and data useful in making optimization recommendations with respect to medical imaging equipment of a health care organization. In one embodiment, the system hardware platform is a workstation which includes a processor coupled to a keyboard so that a user can provide data and commands to the processor. The processor also is coupled to a display and a printer for providing outputs to the user. The workstation also includes a memory coupled to the processor and, as described below in more detail, data utilized in connection with analysis and report generation is stored in the memory.

The processor is programmed to execute a number of operations relating to report generation. More particularly, data related to a particular site is collected, and the data typically relates to the equipment, or inventory, present at the site as well as the various types of procedures, and the number of procedures, performed at the site. After collecting the necessary data, the system then determines, or calculates, various summaries, assessments, capacity utilization, needs assessment, needs comparison, equipment requirements comparison, and procedural efficiency. After making such determinations, the system builds and formats various reports and graphs for presenting the determinations to the user. The data presented in the reports and graphs can then be used to generate optimization recommendations.

The system described above facilitates collection of the necessary data to enable a health care organization better understand its operations and equipment, and also generates various reports so that such an organization can focus its efforts on improving efficiency and planning for future needs.

DETAILED DESCRIPTION OF THE INVENTION

Figure 1:
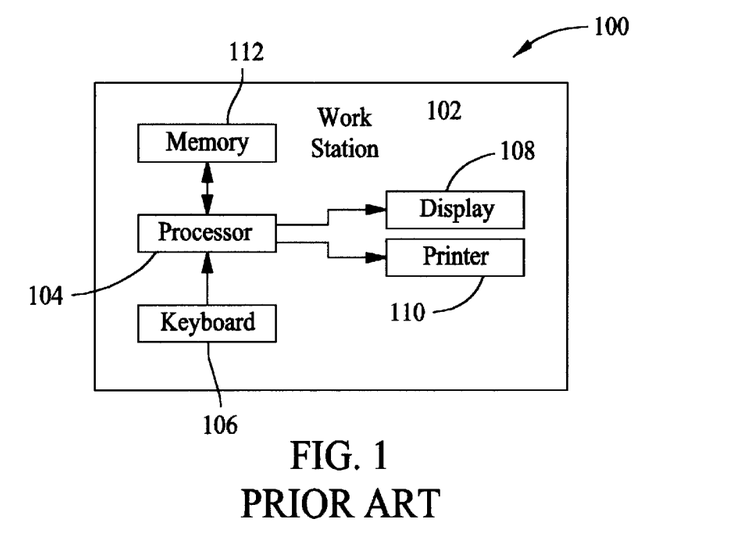
FIG. 1 is a block diagram of a system configured in accordance with one embodiment of the present invention.

FIG. 1 is a block diagram of a system 100 configured in accordance with one embodiment of the present invention.

System 100 is shown as being a workstation 102 and could, for example, be a workstation in the Vectra line of workstations commercially available from Hewlett-Packard Company, Palo Alto, Calif. Of course, many other workstations and other types of computers could be utilized in carrying out the processes described herein and system 100 is shown by way of example only. System 100 includes a processor 104 coupled to a keyboard 106 so that a user can provide data and commands to processor 104. Processor 104 also is coupled to a display 108 and to a printer 110 for providing outputs to the user. Workstation 102 also includes a memory 112 coupled to processor 104 and, as described below in more detail, data utilized in connection with analysis and report generation is stored in memory 112. Commercially available software for generating spreadsheets, such as Microsoft Excel and Microsoft Power Point 2, can be loaded into workstation 102 and utilized in connection with the report generation which is described below in more detail.

Figure 2:
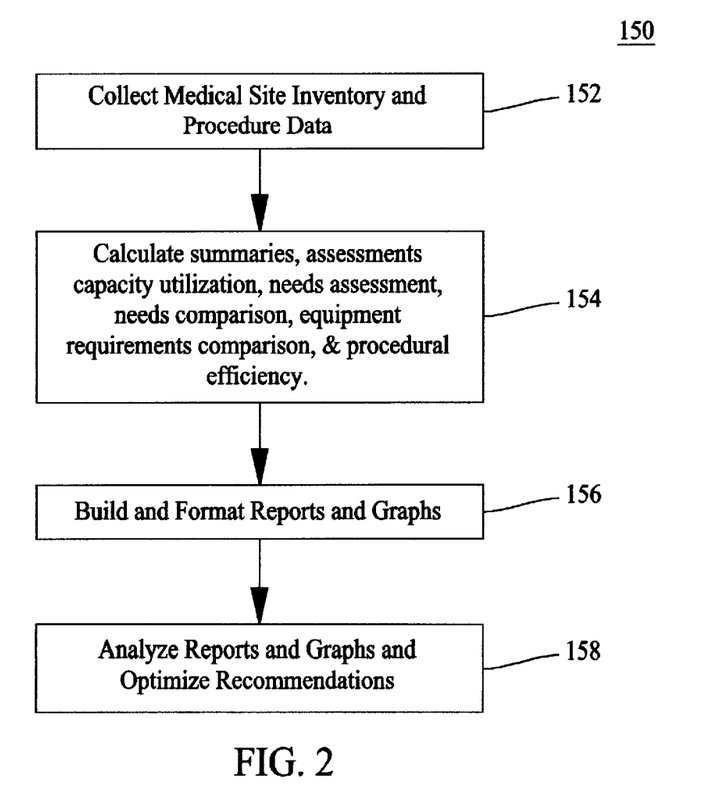
FIG. 2 is a flow chart illustrating a sequence of steps performed in carrying out certain aspects of the present invention.

FIG. 2 is a flow chart 150 illustrating a sequence of steps executed by system 100 (FIG. 1) in carrying out certain aspects of the present invention. As shown in FIG. 2, data related to a particular site is collected 152 such as by prompting the user (e.g., via a display screen on display 108) to input selected data. The data typically relates to the equipment, or inventory, present at the site as well as the various types of procedures, and the number of procedures, performed at the site.

After collecting the necessary data, system 100 operates to determine, or calculate, various summaries, assessments, capacity utilization, needs assessment, needs comparison, equipment requirements comparison, and procedural efficiency 154. After making such determinations, system 100 builds and formats various reports and graphs for presenting the determinations to the user 156. System 100 also analyzes the reports and graphs and generates optimization recommendations 158. System 100 as described above not only facilitates collection of the necessary data to enable a health care organization to better understand its operations and equipment, but also generates various reports and optimization recommendations so that such an organization can focus its efforts on improving efficiency and planning for future needs.

Set forth below in connection with FIGS. 3A, 3B, 4, and 5 are more detailed descriptions of the steps referenced above in connection with FIG. 2. Although specific implementation details are provided, it should be understood that each of the various steps can be implemented in a number of alternative manners and that practicing the present invention is not necessarily limited to carrying out each of the steps in the identical manner as set forth below.

Figure 3A:
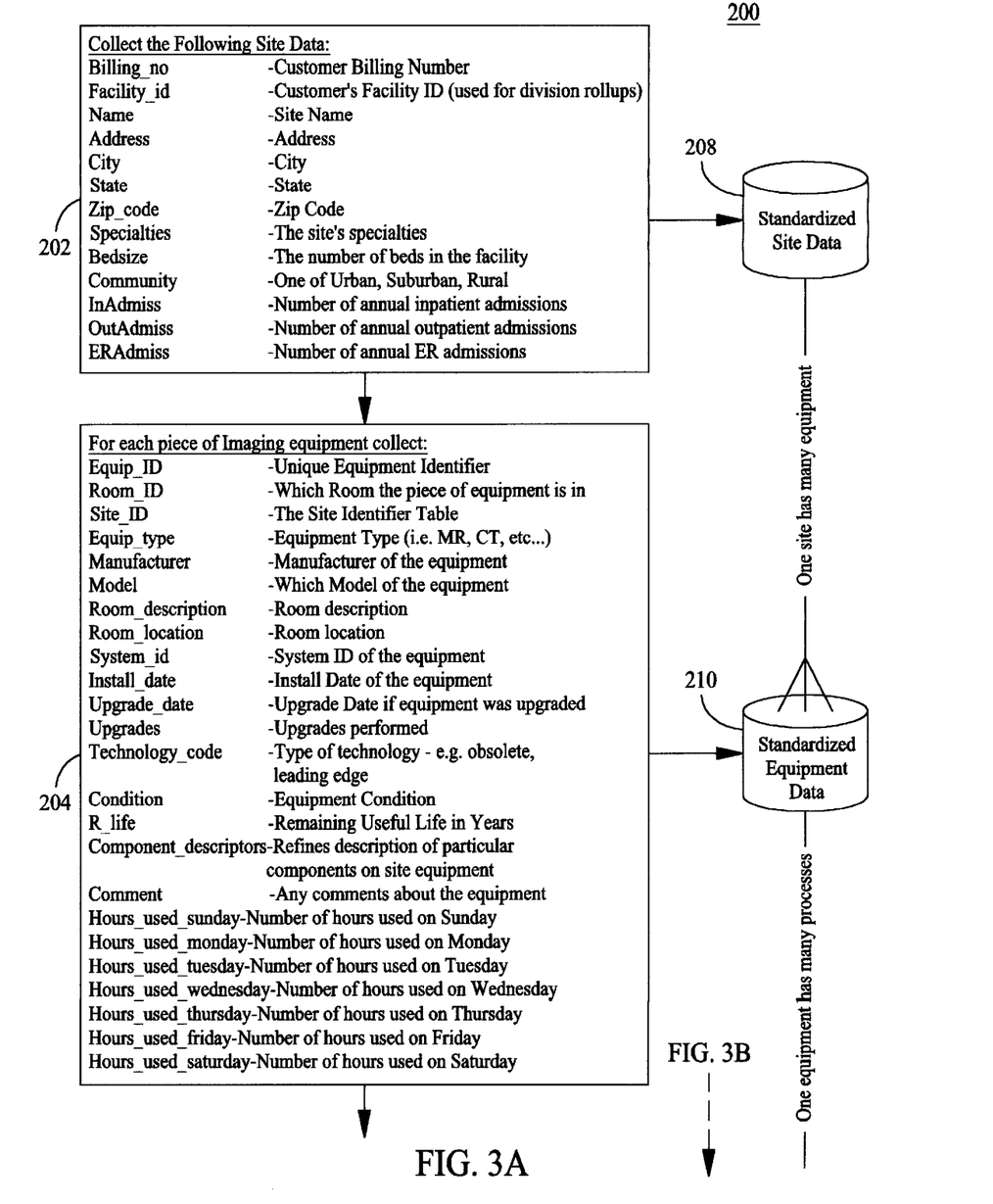
FIGS. 3A and 3B are a flow chart illustrating data collection in accordance with one embodiment of the present invention.
Figure 3B:
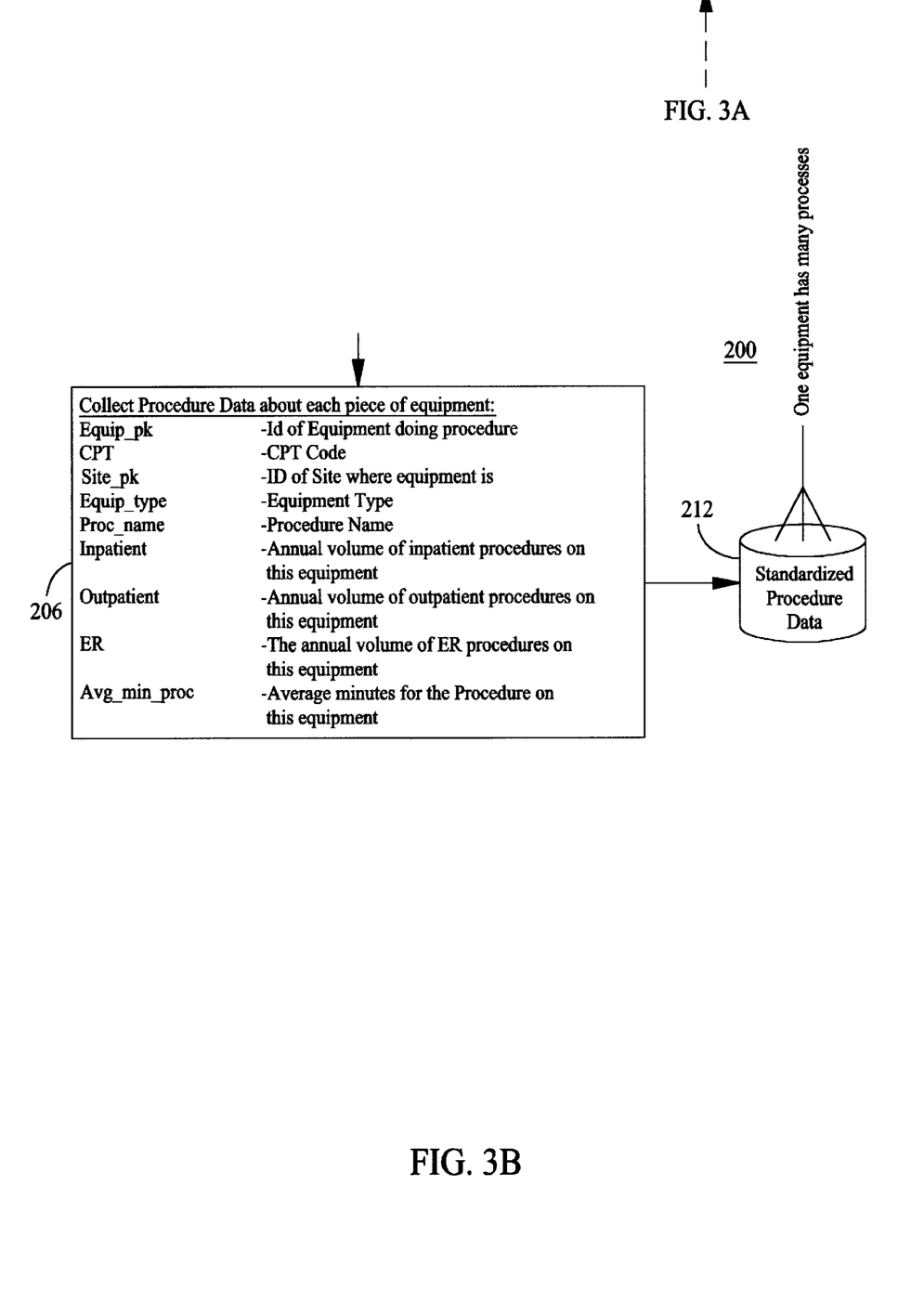

More particularly, FIGS. 3A and 3B are a flow chart 200 illustrating data collection in accordance with one embodiment of the present invention. As shown in FIGS. 3A and 3B, processor 104 generates various screen displays to enable a user to input data elements, and the input data elements are then stored in memory. Particularly, the user is prompted to input data related to the site 202, to each piece of imaging equipment 204, and to procedures performed with respect to each piece of equipment 206. The types of data, or queries, for the site, equipment, and procedures are identified in FIGS. 3A and 3B in each respective block 202, 204, and 206.

In addition, and still referring to FIGS. 3A and 3B, the site data is shown as being stored in a standardized site data base 208, the equipment data is shown as being stored in a standardized equipment data base 210, and the procedure data is shown as being stored in a standardized procedure data base 212. Although separate data bases 208, 210, and 212 are shown in FIGS. 3A and 3B, it should be understood that the data could be collectively stored in memory 112 (FIG. 1) and separate data bases are not necessarily required. In addition, in the illustrated embodiment, the manner in which the data is collected and stored is hierarchical in that one site has many pieces of equipment, and many procedures can be performed on one piece of equipment. Collecting, or at least organizing, the data in this hierarchical format is believed to facilitate the further processing which is described below.

Figure 4:
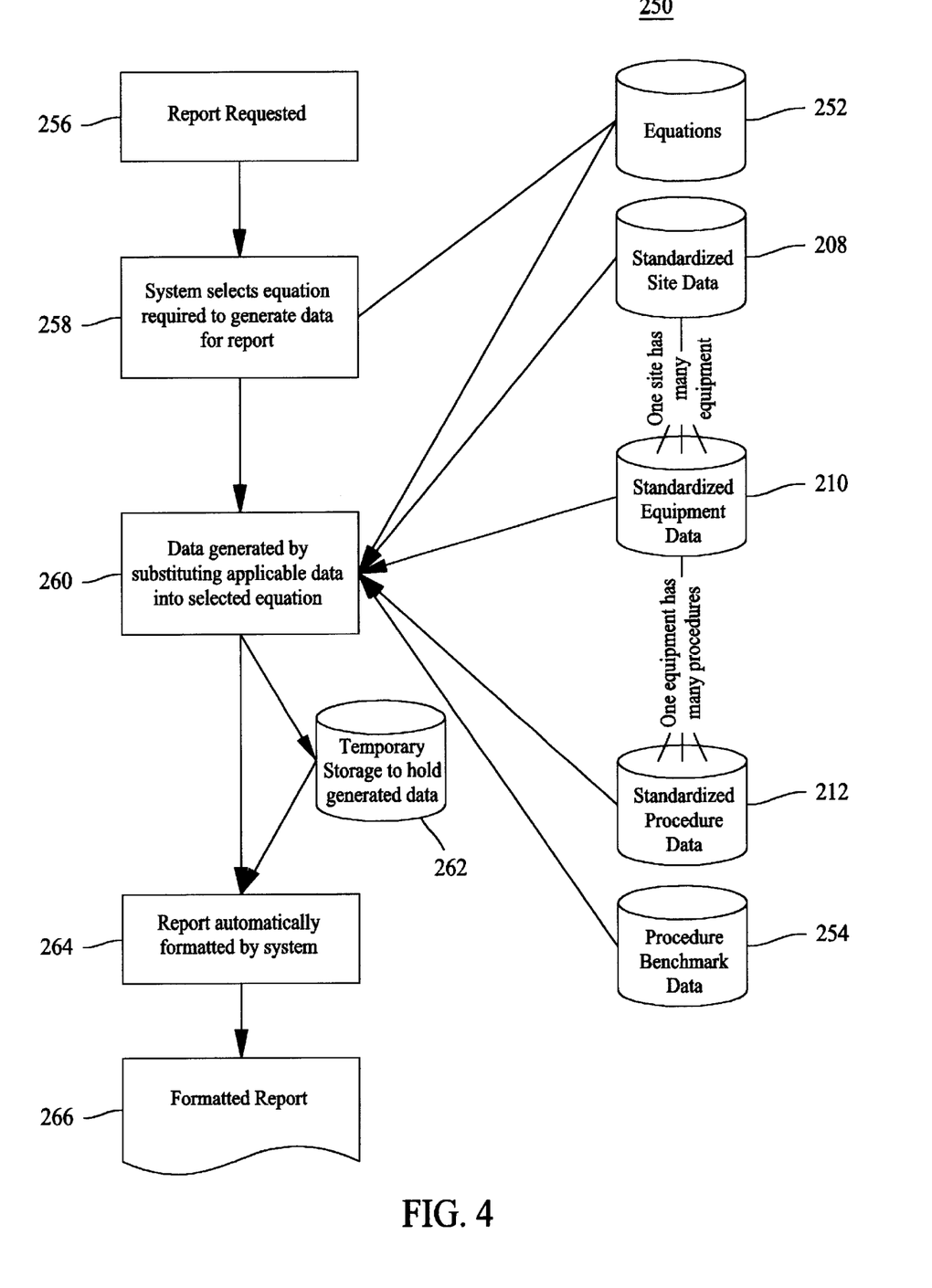
FIG. 4 is a flow chart illustrating report generation in accordance with one embodiment of the present invention.

Once the data is collected and stored as shown in FIGS. 3A and 3B, a user may request that system 100 generate a particular report as shown in FIG. 4. Referring to FIG. 4 which is a flow chart 250 for report generation, and as explained above, standardized site data 208, equipment data 210 and procedure data 212 is stored in memory. In addition, various equations (execution commands) 252 also are stored in memory 112 and procedure benchmark data 254 also is stored in memory 112. With respect to the benchmark data, such data can be generated by the health care organization itself as standards against which it desires to measure itself, or the data can be collected through various industry organizations or questionnaires.

With respect to equations 252, set forth in Appendix A is a table defining the equations/statements that may used in generating reports. Reports which can be generated include a facility inventory summary, a facility inventory assessment, a market inventory summary, a market inventory assessment, a facility inventory condition, a market inventory condition, a facility inventory age, a market inventory age, a facility inventory technology, a market inventory technology, a facility actual capacity utilization, a market actual capacity utilization, a facility potential capacity utilization, an average annual procedures, an average annual procedures per unit, an equipment needs assessment, a procedural efficiency, a facility capacity utilization benchmarking, and an equipment needs comparison report. Of course, system 100 can be configured to generate fewer or more reports, and the specific manner in which such reports are generated can vary.

In the table set forth in Appendix A, the first column identifies the specific type of report to be produced, and the middle column sets forth the computer language statements that generate the data needed to produce the report. The statements are written in Structured Query Language (SQL). The SQL used in the appendix is ANSI-89 Level 1 compliant, and is an accepted language for the manipulation of data organized in a relational data model. SQL is also recognized as computer language that implements operations in set theory. The third column is a description of the SQL equations and statements set forth in the middle column.

Referring again to FIG. 4, once a user inputs a report request 256, processor 104 selects 258 an equation 252 required to generate data for the requested report. The data is then generated 260 by processor 104 by using the site data, equipment data, and procedure data, and the applicable equation. The generated data may be temporarily stored in selected memory locations (shown as a database 262) while other data is generated. Processor 104 then automatically formats the report 264 and the formatted report is then displayed on display 108 and/or printed out 266 on printer 110 for the user to review. Exemplary reports are described hereinafter in more detail.

Figure 5:
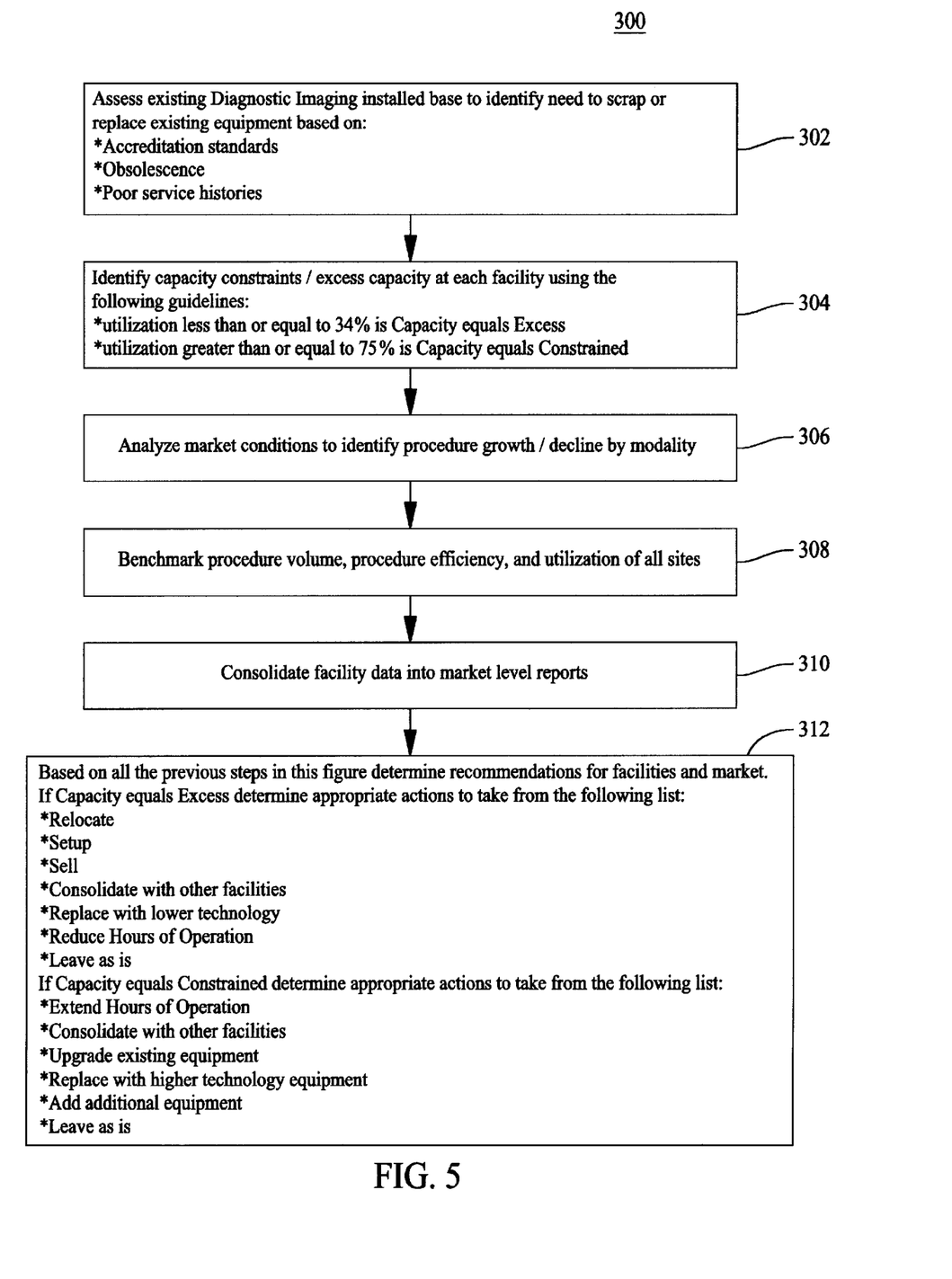
FIG. 5 is a flow chart illustrating generation of optimization recommendations in accordance with one embodiment of the present invention.

FIG. 5 is a flow chart 300 illustrating the process for generating optimization recommendations in accordance with one embodiment of the present invention. Referring specifically to FIG. 5, a user assesses imaging equipment at a particular site, or base, to identify a need to scrap or replace existing equipment 302. In this embodiment, such recommendations are made utilizing accreditation standards, obsolescence data, and service histories. The specific accreditation standards, obsolescence data, and service histories may vary from state to state, modality to modality, and service organization to service organization. The data bases can be created using well known data base generation programs, and the analysis of such data against the accreditation, obsolescence and service histories is straight forward. For example, if a particular piece of equipment fails to meet the basic accreditation standards, or is obsolescent as determined by industry standards, or has a very poor service history, then the recommendation may be to scrap or replace the particular piece of equipment.

After making the above described assessment, the user then identifies any capacity constraints or excess capacity at each facility 304. In this embodiment, a set of rules is used in making such determinations. Particularly, if the utilization of a particular piece of imaging equipment is less than or equal to 34% of the equipment capacity, then the capacity is identified as being "excess" capacity. If the utilization of a particular piece of imaging equipment is greater than or equal to 75%, then the capacity is identified as being "constrained". Of course, the particular percentages can vary by location, modality, and equipment manufacturer. Once the assessment and capacity are determined as described above, the user then analyzes market conditions to determine procedure growth or decline by modality 306.

Benchmark procedure volume, procedure efficiency, and utilization data is then supplied 308 to system 100 for each site. This benchmark data is utilized by system 100, as described below in more detail, to generate reports which enable the user to compare its operations to the selected benchmarks. The facility data is then consolidated into market level reports 310 by system 100. The generation commands for such reports are set forth in Appendix A, referenced above, and some of such reports are described hereinafter in more detail.

Recommendations can then be generated 312 by the user using the reports. For example, if capacity is "excess", then appropriate actions may include at least one of relocate, scrap, sell, consolidate, replace, reduce operation hours, or leave the facility "as is". If capacity is "constrained", then appropriate actions may include at least one of extend hours of operation, consolidate with other facilities, upgrade existing equipment, replace equipment with higher technology equipment, add additional equipment, or leave the facility "as is".

Figure 6:
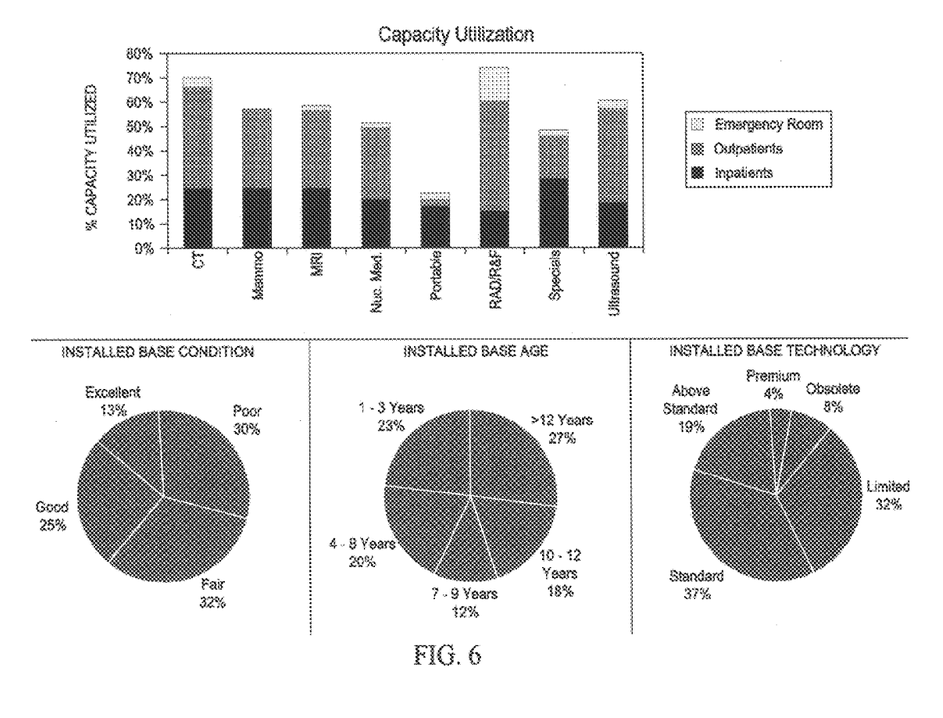
FIG. 6 is an exemplary report generated by the system described herein to illustrate various aspects of equipment utilization, condition, age, and technology.

FIG. 6 is an exemplary report generated by system. Particularly, the capacity utilization by modality and basis (e.g., emergency room, outpatient, inpatient) is shown. Further, the installed base condition (qualitative), the installed base age (quantitative), and the installed base technology condition (e.g., obsolete to premium) is shown.

Figure 7:
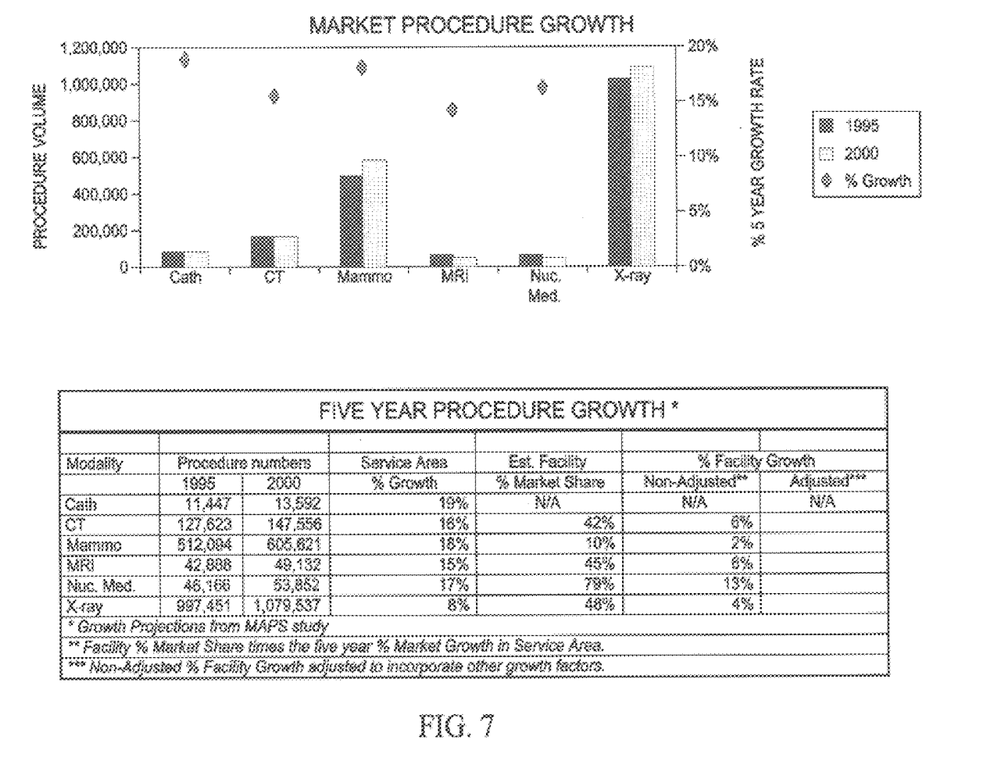
FIG. 7 illustrates exemplary procedure growth data supplied to the system.

FIG. 7 is an exemplary market growth report generated by a user, and the data contained in the report is supplied to system 100. Particularly, the current procedure volume and the anticipated 5 year growth rate are shown by modality.

Figure 8:
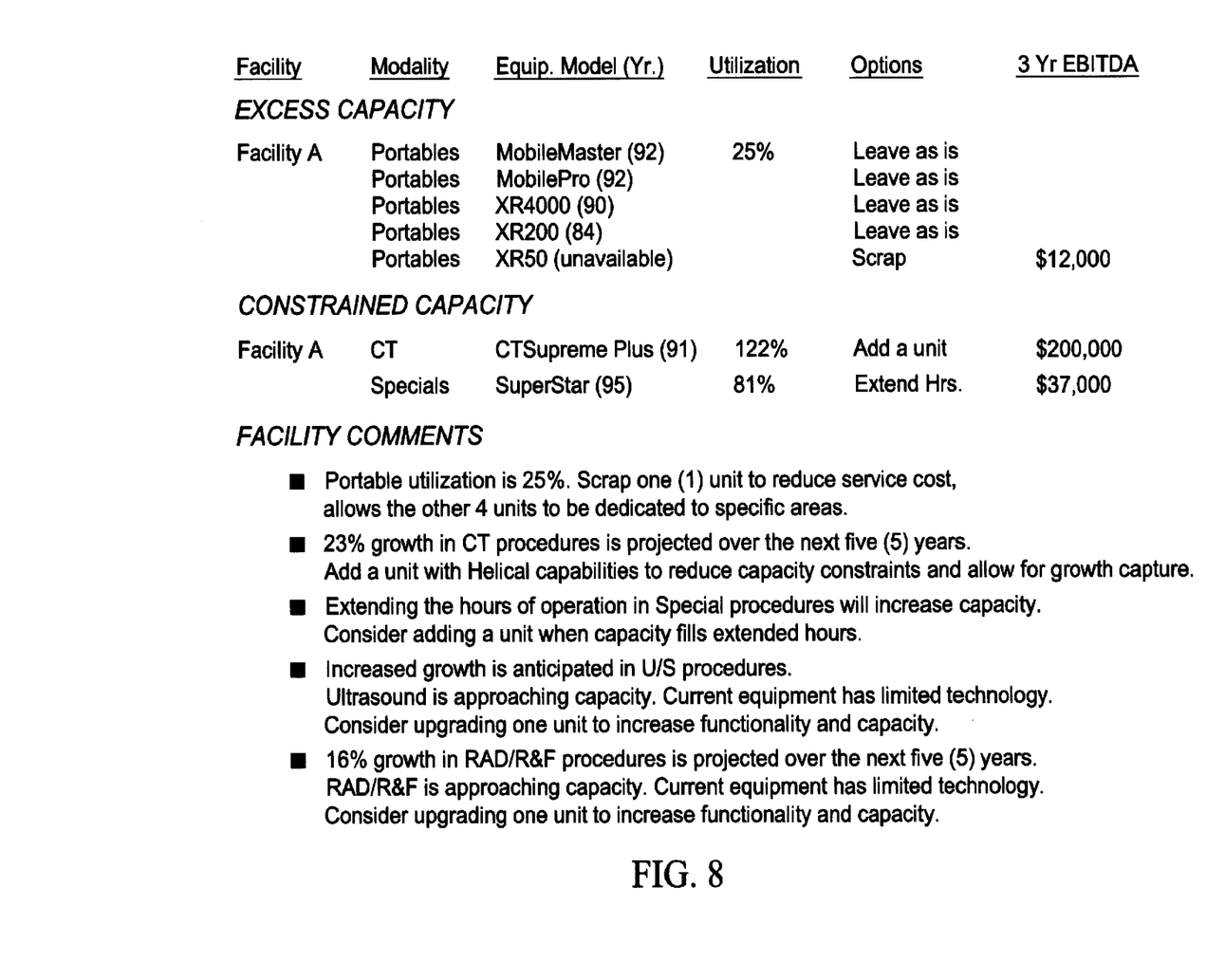
FIG. 8 is an exemplary report generated by the system described herein to illustrate various aspects of equipment capacity

FIG. 8 is an exemplary report generated by system with respect to equipment capacity. The capacity is generally categorized as "excess" or "constrained" as identified above.

As shown in FIG. 8, a block designation is provided to enable facility comments to be input on this report.

Figure 9:
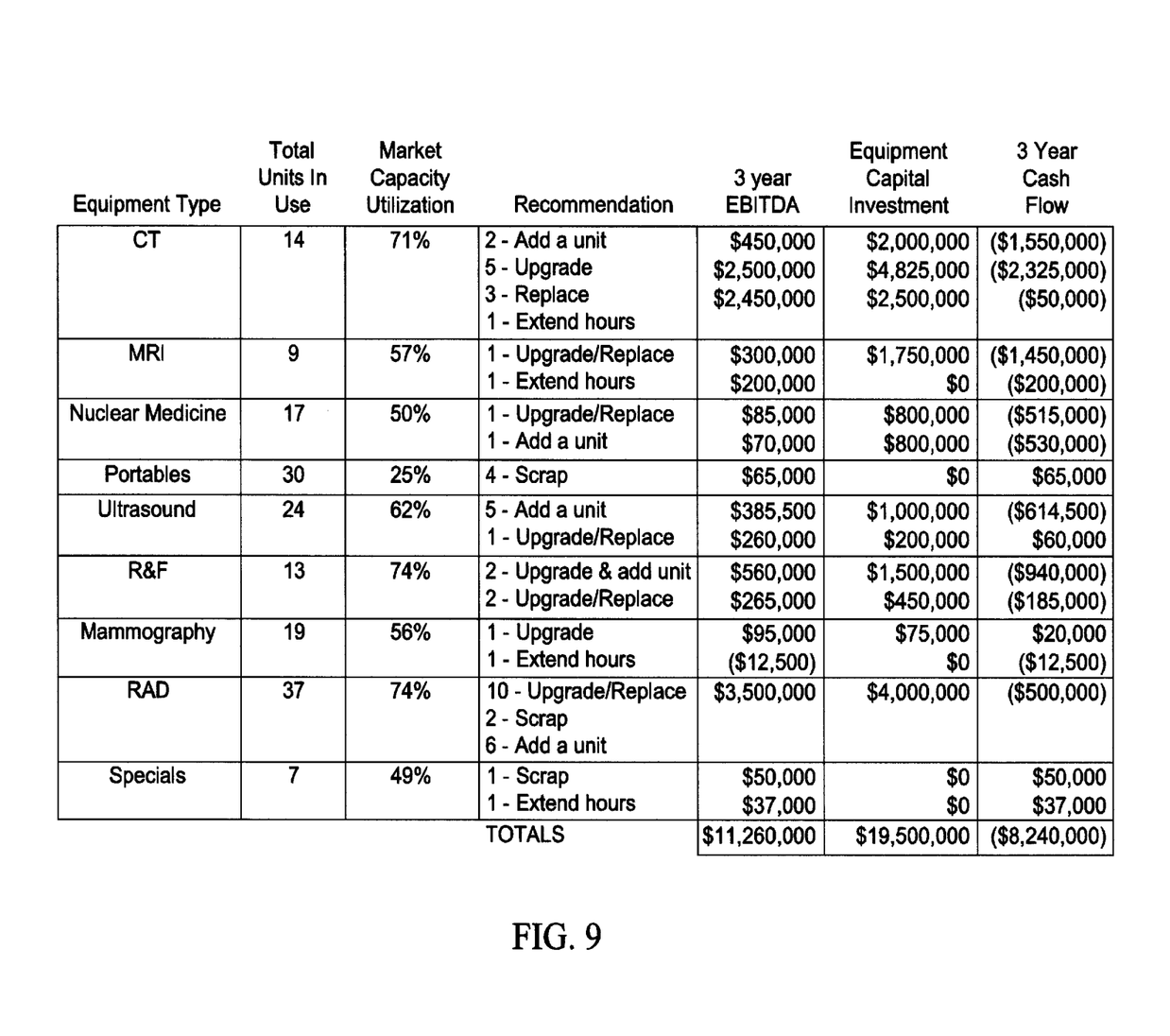
FIG. 9 is an exemplary report generated by the system described herein to illustrate various aspects of future needs by modality.

FIG. 9 is an exemplary report generated by system for making recommendations based on equipment capacity. As shown, the recommendations include "add a unit", "upgrade", "replace", "extend hours", "scrap", and combinations thereof. The 3 year earnings before interest, taxes, depreciation, and amortization ("3 Year EBITDA"), equipment capital cost and a cash flow analysis may also be included.

Figure 10A:
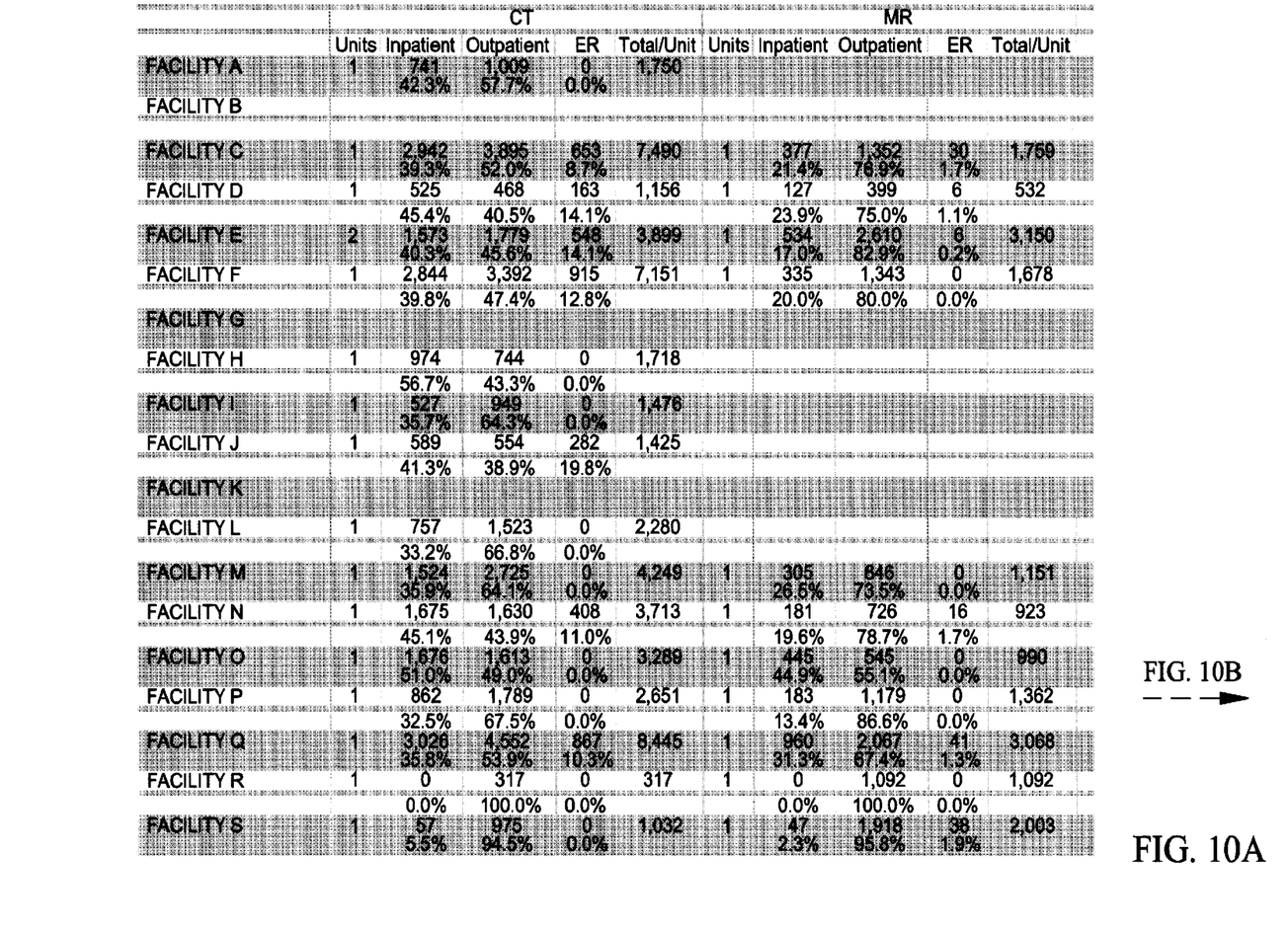
FIGS. 10A and 10B are an exemplary report generated by the system described herein to illustrate various aspects of procedures performed by facility and type.
Figure 10B:
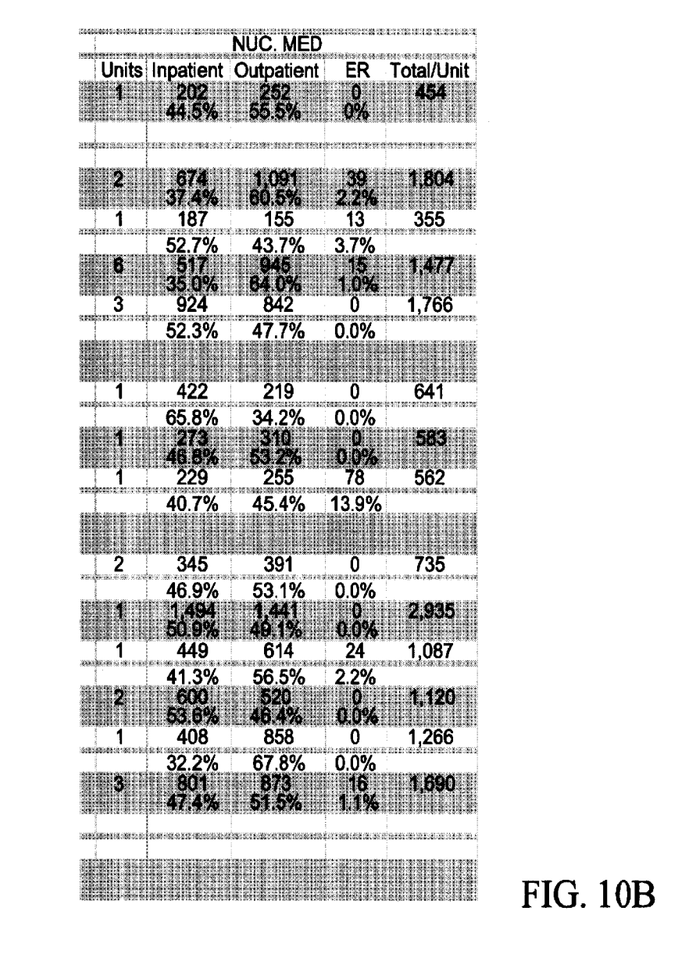

FIGS. 10A and 10B are an exemplary report generated by system to illustrate various aspects of procedures performed by facility and type. Some of this data is illustrated in an alternative form, but only for one facility, in FIG. 6. This report enables an organization to quickly understand equipment usage by facility and the basis (e.g., inpatient, outpatient, and ER on which such equipment is used.

Figure 11:
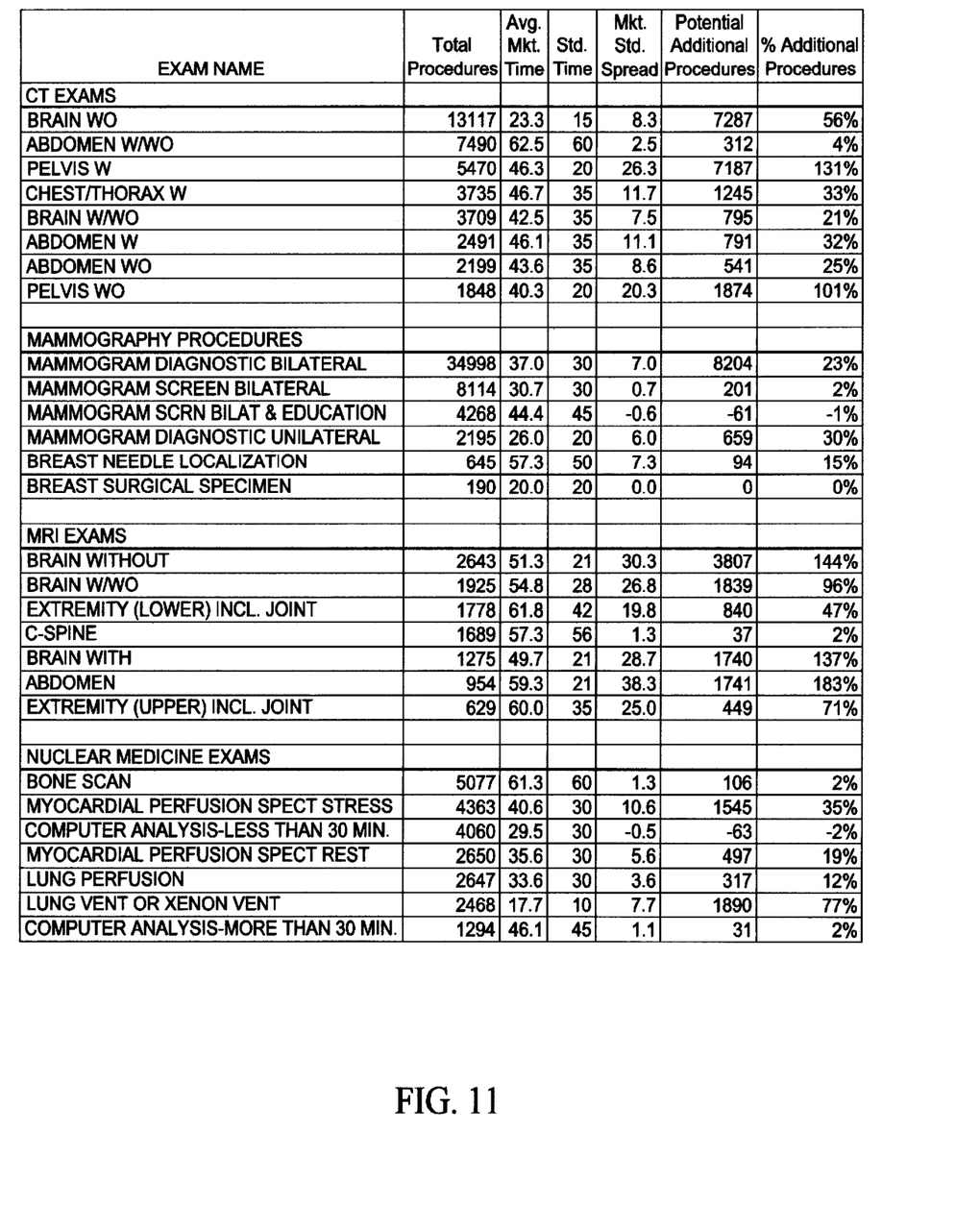
FIG. 11 is an exemplary report generated by the system described herein to illustrate various aspects of procedures performed by procedure type and modality.

FIG. 11 is an exemplary report generated by system to illustrate various aspects of procedures performed by procedure type and modality. The report shown in FIG. 11 also includes benchmarking type data so that the organization can evaluate itself against selected benchmarks.

Figure 12A:
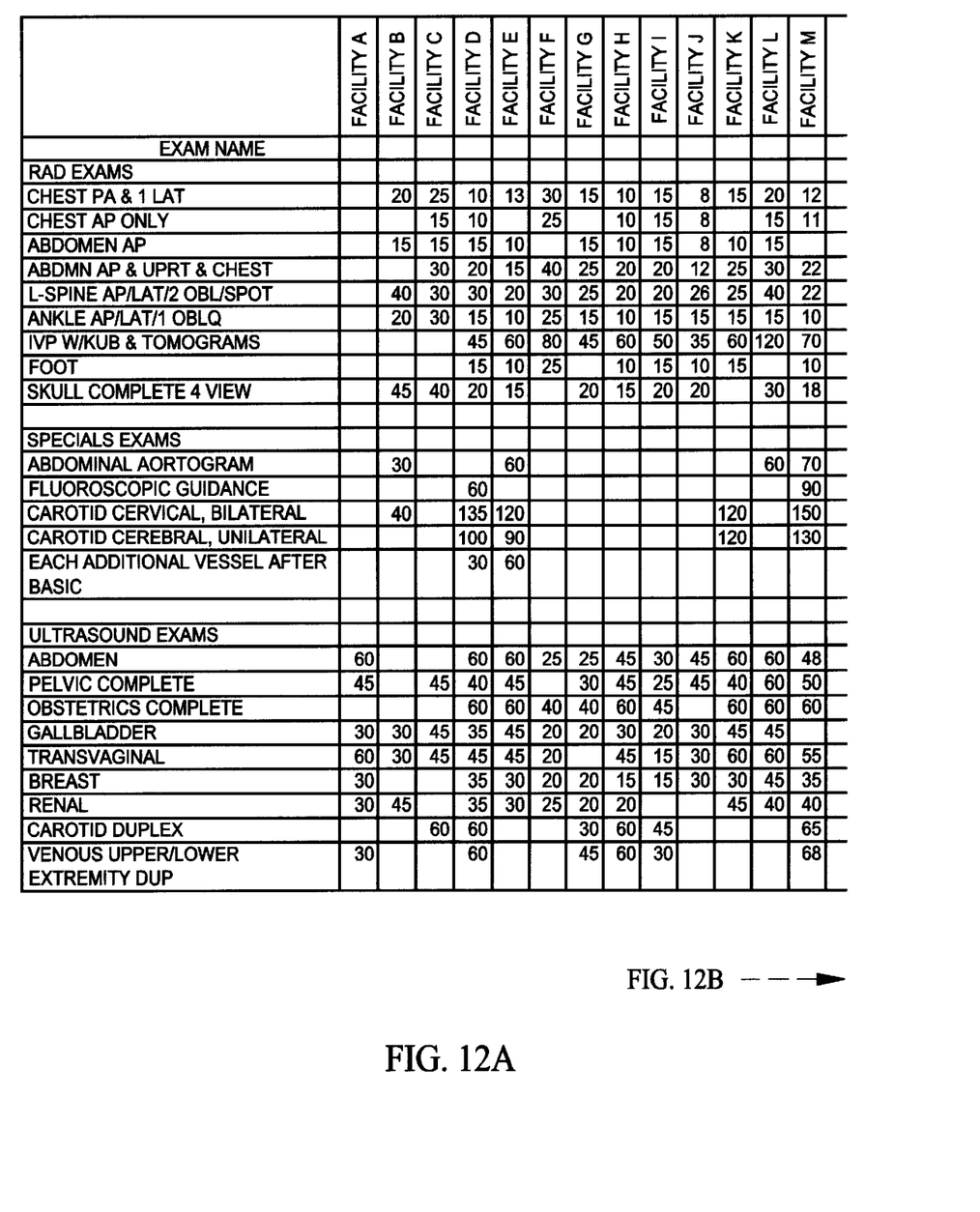
FIGS. 12A and 12B are an exemplary report generated by the system described herein to illustrate various aspects of procedures performed by procedure type and facility.
Figure 12B:
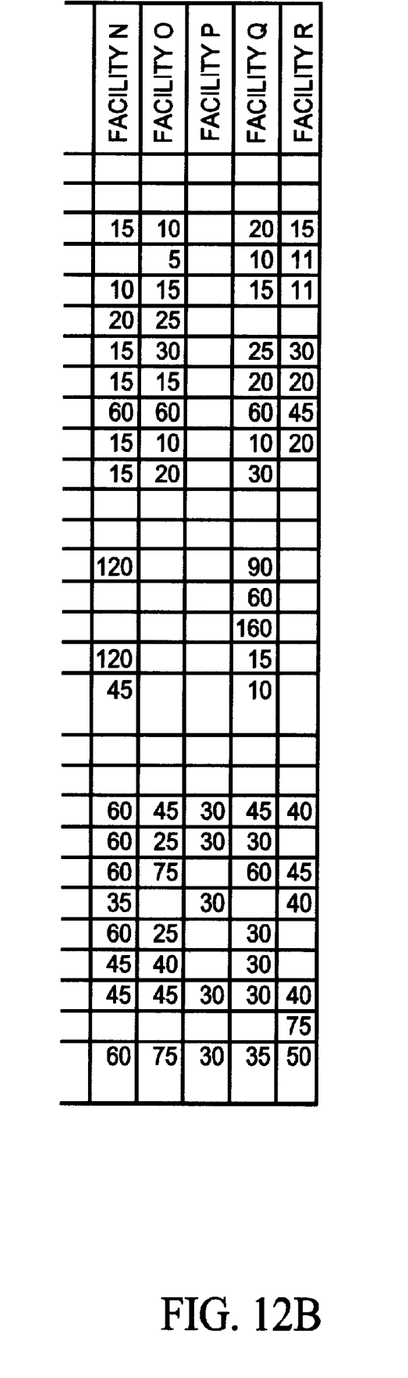

FIGS. 12A and 12B are an exemplary report generated by system to illustrate various aspects of procedures performed by procedure type and facility. This type of report provides an in-depth understanding of the types of procedures and cycle times of procedures being performed at various facilities within the health care organization.

The systems and methods described above facilitate collection of the necessary data to enable health care organizations better understand their operations and equipment, and also generate various reports and optimization recommendations so that such organizations can focus efforts on improving efficiency and planning for future needs. Further, the systems and methods are not believed to be overly complex nor costly so that such systems and methods can be easily and quickly utilized within such organizations.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A method for utilizing medical imaging system equipment in a health care facility, said method comprising:

collecting inventory data relating to imaging system inventory of a health care facility, the inventory data including data for each piece of imaging equipment;

collecting utilization data relating to imaging system procedure volume and time required to perform imaging procedures, the utilization data relating to imaging system procedure volume and time including data for each piece of imaging equipment;

producing optimization recommendations substantially on the basis of said inventory and utilization data, utilizing a computerized relational database system to produce the optimization recommendations; and at least one of relocate equipment, scrap equipment, sell equipment, consolidate equipment with other facilities, replace equipment, reduce operating hours, extend operating hours, upgrade existing equipment, and add additional equipment, in accordance with the optimization recommendations.

2. A method in accordance with claim 1 wherein optimization recommendations based substantially on said inventory and utilization data comprises:

determining imaging system equipment utilization at the health care facility; and comparing the calculated utilization to utilization in other health care facilities, utilizing the relational database system, to determine surpluses or shortages of imaging equipment.

3. A method in accordance with claim 2 wherein calculating imaging system equipment utilization at the health care facility comprises using a program of the relational database system to calculate a total number of imaging systems required, a difference between a number of existing imaging systems and the number of imaging systems required, and a difference between a number of imaging systems in use and the number of imaging systems required.

4. A method for utilizing medical imaging system equipment in a health care facility, said method comprising:

maintaining an inventory and utilization record of medical imaging systems of a health care facility in a relational database system, the inventory and utilization record including data for each piece of imaging equipment;

producing recommendations for the health care facility for future medical imaging system utilization and equipment needs utilizing the relational database system, wherein said recommendations are substantially based upon the inventory and utilization record of the medical imaging systems, and at least one of relocate equipment, scrap equipment, sell equipment, consolidate equipment with other facilities, replace equipment, reduce operating hours, extend operating hours, upgrade existing equipment, and add additional equipment, in accordance with the optimization recommendations.

5. A method in accordance with claim 4 wherein maintaining an inventory and utilization record of medical imaging systems in the health care facility comprises maintaining records relating to numbers of procedures and procedure times for each of the medical imaging systems at the health care facility.

6. A method in accordance with claim 5 wherein producing recommendations for future utilization and equipment needs and basing said recommendations substantially upon the inventory and utilization record of the medical imaging system includes using a program of the relational database system to generate comparisons of utilization and procedure times for the medical imaging systems of the health care facility to standarized utilization and procedure times.

7. A method in accordance with claim 6 wherein producing recommendations for future utilization and equipment needs and basing said recommendations substantially upon the inventory and utilization record of the medical imaging system includes using a program of the relational database system to generate comparisons of utilization and procedure times for the medical imaging systems of the health care facility to utilization and procedure times of medical imaging systems within a market served by the health care facility.

8. A method for utilizing medical imaging system equipment in a health care facility, said method comprising:

maintaining an inventory and utilization record of medical imaging systems of a health care facility in a relational database system, the inventory and utilization record including data for each piece of imaging equipment;

producing recommendations for the health care facility for future medical imaging system utilization and equipment needs utilizing the relational database system, wherein said recommendations are substantially based upon the inventory and utilization record of the medical imaging system, accreditation standards, obsolescence data, and service history; and at least one of relocate equipment, scrap equipment, sell equipment, consolidate equipment with other facilities, replace equipment, reduce operating hours, extend operating hours, upgrade existing equipment, and add additional equipment, in accordance with the optimization recommendation.

9. A method in accordance with claim 8 wherein maintaining an inventory and utilization record of medical imaging systems of a health care facility comprises identifying medical imaging equipment as either having excess or constrained capacity, depending upon a percentage utilization of the medical imaging equipment.

10. A method in accordance with claim 9 wherein producing recommendations for future utilization and equipment needs and basing said recommendations substantially upon the inventory and utilization record of the medical imaging systems, accreditation standards, obsolescence data, and service history includes comparing operations of the health care facility to benchmark data utilizing the relational database system.

11. A method in accordance with claim 7 wherein the recommendations include recommendations to change operating hours.

12. A method in accordance with claim 7 further comprising maintaining an inventory and utilization record of medical imaging systems of a plurality of health care facilities in the relational database system.

13. A method for utilizing medical imaging system equipment in a health care facility, said method comprising:

maintaining an inventory and utilization record of medical imaging systems of a health care facility in a relational database system, the inventory and utilization record including data for each piece of imaging equipment;

producing recommendations for the health care facility for future medical imaging system utilization and equipment needs utilizing the relational database system, wherein said recommendations are substantially based upon the inventory and utilization record of the medical imaging systems;

at least one of relocate equipment, scrap equipment, sell equipment, consolidate equipment with other facilities, replace equipment, reduce operating hours, extend operating hours, upgrade existing equipment, and add additional equipment, in accordance with the optimization recommendation; and generating utilizing the relational database system, reports of medical imaging system capacity utilization by modality and basis.

14. A method in accordance with claim 13 and further comprising generating, utilizing the relational database system, reports of medical imaging system installed base age and installed base technology condition.

* * * * *

UNITED STATES PATENT AND TRADEMARK OFFICE
CERTIFICATE OF CORRECTION

PATENT NO.    : 6,430,536 B2
DATED         : August 6, 2002
INVENTOR(S)   : Irving et al.

It is certified that error appears in the above-identified patent and that said Letters Patent is hereby corrected as shown below:

Column 7,
Line 24, after "including data" insert -- relating to imaging system procedure volume and time --.
Line 30, delete "systems, and" and insert therefor -- systems; and --.

Column 8,
Line 2, after "including data" insert -- relating to imaging system procedure volume and time --.
Line 8, delete "system" and insert therefor -- systems --.
Line 15, delete "recommendation" and insert therefor -- recommendations --.
Line 43, after "including data" insert -- relating to imaging system procedure volume and time --.
Line 55, delete "recommendation" and insert therefor -- recommendations --.
Line 56, after "generating" insert -- , --.

Signed and Sealed this

Ninth Day of November, 2004

JON W. DUDAS
*Director of the United States Patent and Trademark Office*